(12) United States Patent
Perot et al.

(10) Patent No.: US 11,701,470 B2
(45) Date of Patent: Jul. 18, 2023

(54) INJECTION SYSTEM COMPRISING A SYRINGE AND A PROTECTIVE ASSEMBLY

(71) Applicant: Becton Dickinson France, Le Pont de Claix (FR)

(72) Inventors: Frédéric Perot, Saint Paul de Varees (FR); Salim Bouyahiaoui, Annecy (FR); Gilles Bernède, Arbusigny (FR)

(73) Assignee: Becton Dickinson France, Le Pont de Claix (FR)

( * ) Notice: Subject to any disclaimer, the term of this patent is extended or adjusted under 35 U.S.C. 154(b) by 445 days.

(21) Appl. No.: 16/970,821

(22) PCT Filed: Feb. 12, 2019

(86) PCT No.: PCT/EP2019/053467
§ 371 (c)(1),
(2) Date: Aug. 18, 2020

(87) PCT Pub. No.: WO2019/158538
PCT Pub. Date: Aug. 22, 2019

(65) Prior Publication Data
US 2021/0093787 A1   Apr. 1, 2021

(30) Foreign Application Priority Data

Feb. 19, 2018 (EP) .................... 18157458

(51) Int. Cl.
*A61M 5/31* (2006.01)
*A61M 5/315* (2006.01)
*A61M 5/32* (2006.01)

(52) U.S. Cl.
CPC ...... *A61M 5/3129* (2013.01); *A61M 5/31511* (2013.01); *A61M 5/3204* (2013.01)

(58) Field of Classification Search
CPC ...... A61M 5/31511; A61M 2005/3267; A61M 5/31501; A61M 5/502; A61M 5/3129
See application file for complete search history.

(56) References Cited

U.S. PATENT DOCUMENTS

| 7,588,559 B2 | 9/2009 | Aravena et al. |
| 9,199,063 B2 | 12/2015 | Baid |

(Continued)

FOREIGN PATENT DOCUMENTS

| CN | 102512746 A | 6/2012 |
| JP | 20144041 A | 1/2014 |

(Continued)

*Primary Examiner* — Bradley J Osinski
(74) *Attorney, Agent, or Firm* — The Webb Law Firm

(57) ABSTRACT

A protective assembly includes a body for receiving the syringe; and a coupling device inside the body, rigidly connected to the barrel as regards to axial movement relative to the body. The coupling device includes an attaching element which can be either in an engaged state to axially fix the coupling device and the plunger rod, or in a release state in which the coupling device and the plunger rod are axially free relative to one another. The coupling device is axially movable in the body from a storage position to an injection position in which the needle extends beyond the body, and in which the attaching element can move towards the release state. The coupling device is axially movable in the body from the injection position towards a safety position, in which the needle is covered by the body.

19 Claims, 10 Drawing Sheets

(56) References Cited

U.S. PATENT DOCUMENTS

| | | | |
|---|---|---|---|
| 2014/0257184 A1* | 9/2014 | Carrel | A61M 5/3287 |
| | | | 604/117 |
| 2017/0143903 A1 | 5/2017 | Helmer | |
| 2017/0354791 A1 | 12/2017 | Lewkonya et al. | |

FOREIGN PATENT DOCUMENTS

| | | |
|---|---|---|
| WO | 2004032989 A2 | 4/2004 |
| WO | 2004041332 A1 | 5/2004 |

\* cited by examiner

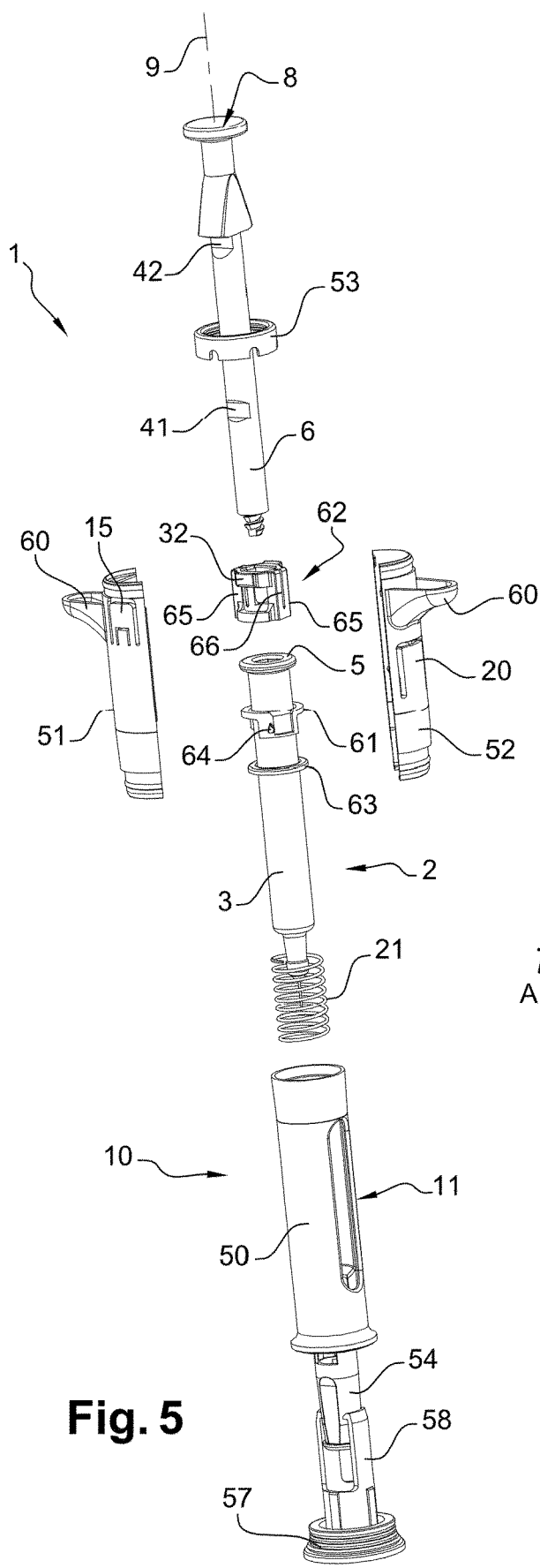
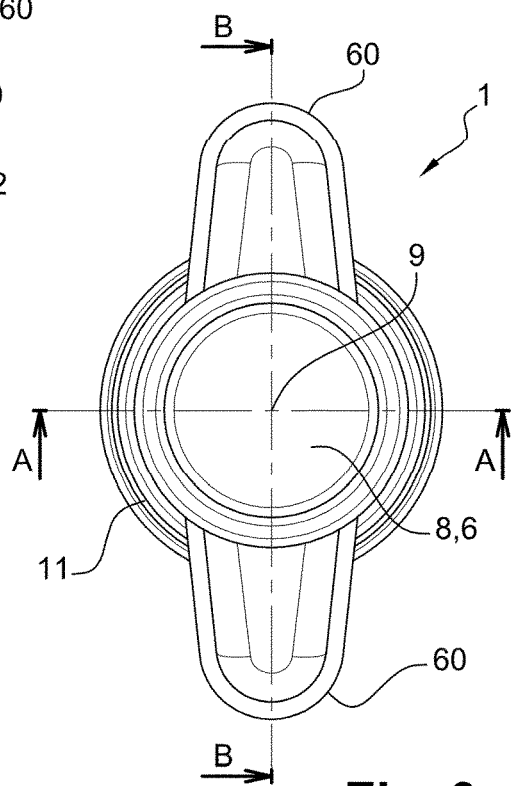
Fig. 5
Fig. 6

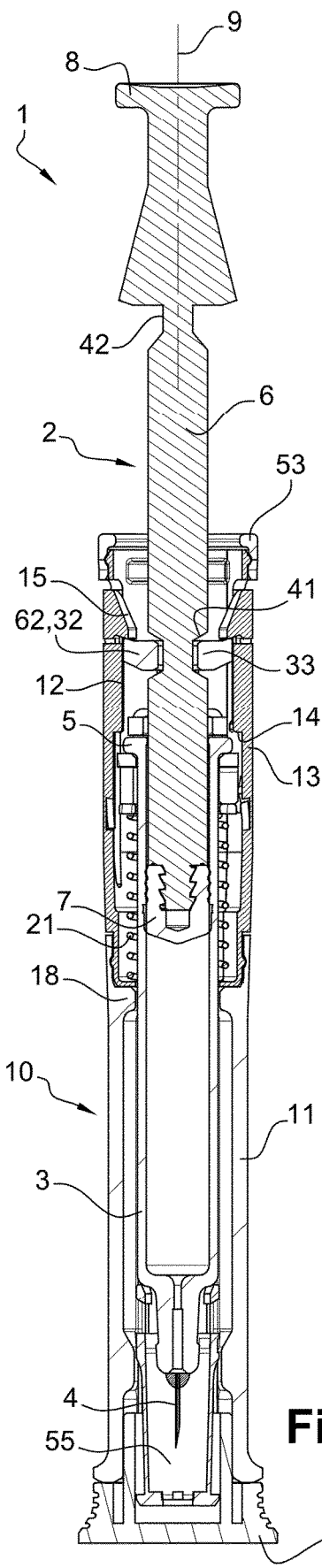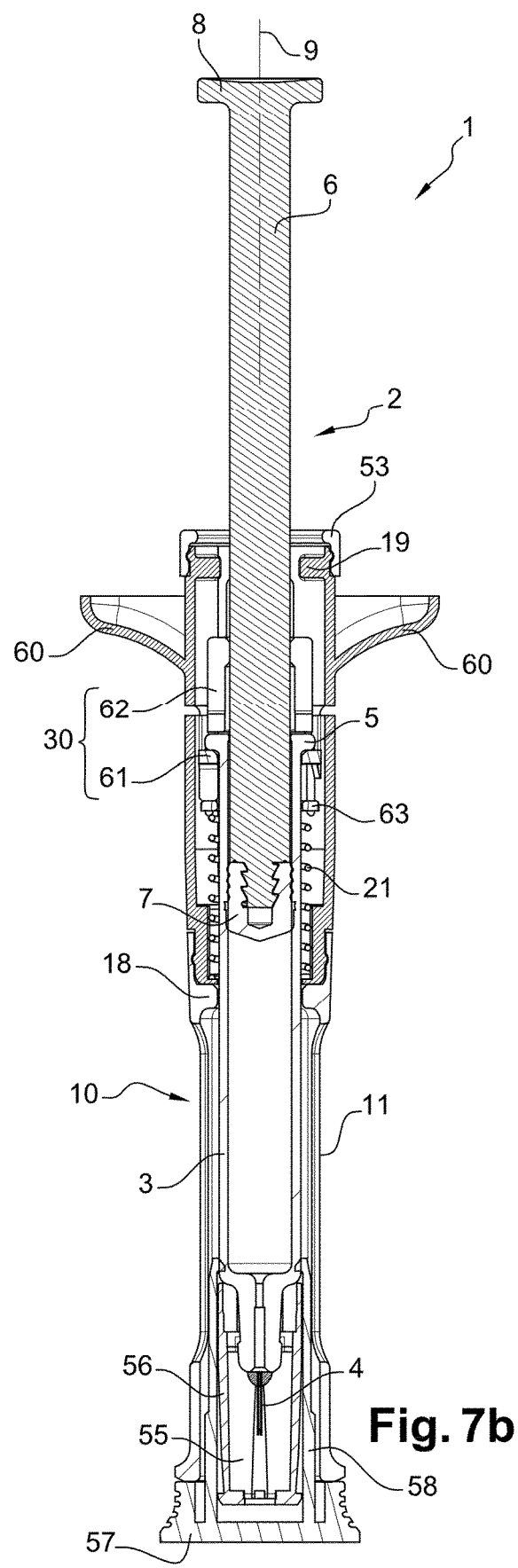

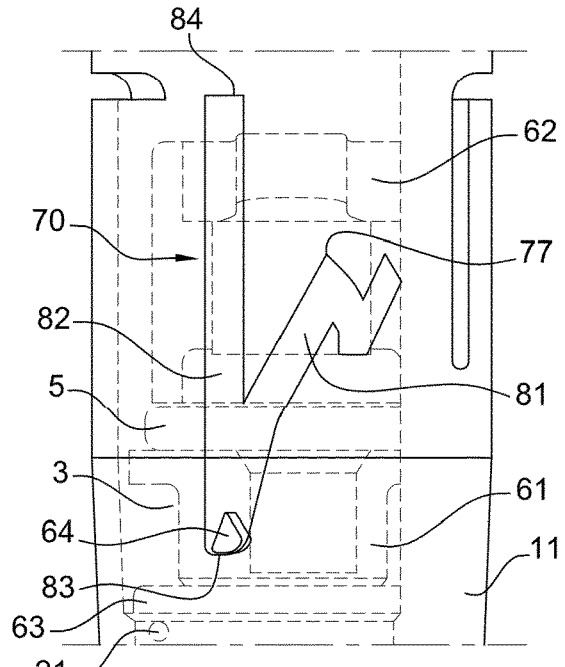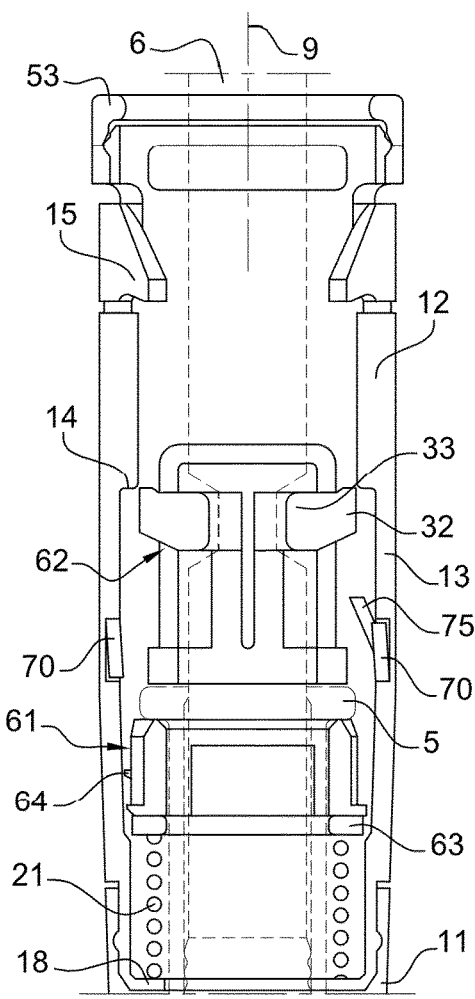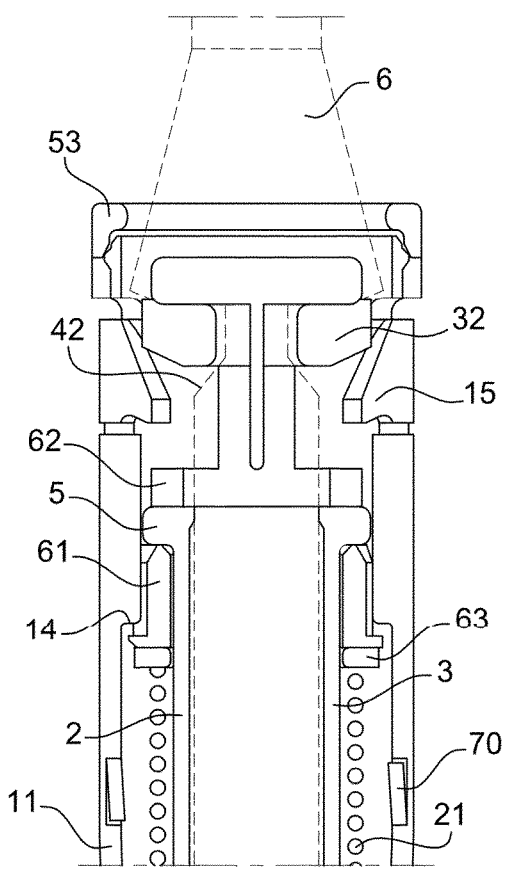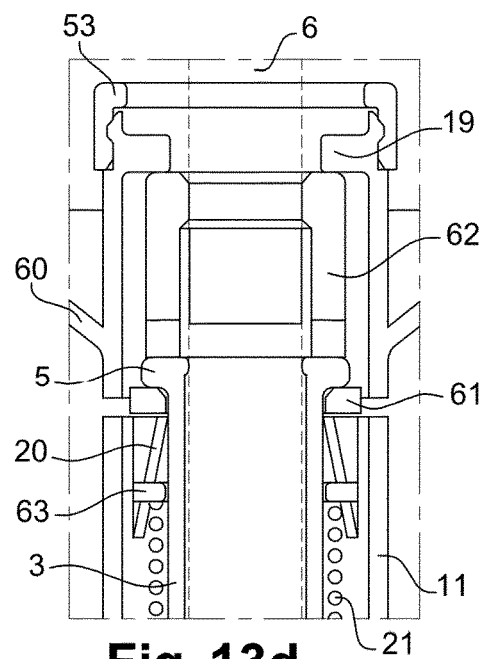

INJECTION SYSTEM COMPRISING A SYRINGE AND A PROTECTIVE ASSEMBLY

CROSS-REFERENCE TO RELATED APPLICATIONS

This application is the United States national phase of International Application No. PCT/EP2019/053467 filed Feb. 12, 2019, and claims priority to European Patent Application No. 18157458.3 filed Feb. 19, 2018, the disclosures of which are hereby incorporated by reference in their entirety.

BACKGROUND OF THE INVENTION

Field of the Invention

The invention relates to a protective assembly for a syringe, to an injection system comprising a syringe and such a protective assembly, and to a process for operating such an injection system.

Description of Related Art

Some illnesses, such as multiple sclerosis or arthritis, necessitate that a drug be injected into a patient regularly, such as every day or every week. The drug is available under the form of prefilled drug delivery devices, such as prefilled syringes.

Usually, the patient is trained to self injection and is capable to proceed to the injection of the drug by himself. Nevertheless, injection systems are provided to make injection easier for the patient.

Injections systems thus aim at ensuring injection is carried out properly, at increasing safety especially regarding accidental needle stick injury, and at reducing the patient's apprehension.

Although known injections systems are generally satisfactory, they do not always meet all of the user's expectations. In particular, they may be fairly difficult to use when they require successive different movements of the hands to complete the pricking and injection steps. Besides, they do not allow stopping the injection, which may be desired by some patients, for example when injection is painful, and resume injection while ensuring both complete safety and impeccable quality of injection.

SUMMARY OF THE INVENTION

There is therefore a need for an improved injection system that would make self injection even easier, safer, and less difficult emotionally.

To that end, according to a first aspect, the invention relates to a protective assembly for a syringe comprising a barrel, a plunger rod and a needle, the protective assembly having an axis and comprising:
- a body for receiving the syringe;
- a coupling device arranged inside the body, configured to be rigidly connected to the barrel as regards axial movement relative to the body, the coupling device comprising an attaching element or attaching means which are configured to be either in an engaged state with the plunger rod in order to axially fix the coupling device and the plunger rod, or in a release state in which the coupling device and the plunger rod are axially free relative to one another, wherein the coupling device is axially movable in the body:
- from a storage position, distally along a first travel distance along which the attaching element or attaching means are in the engaged state, to an injection position in which the needle extends beyond the body, and in which the attaching element or attaching means are free to move towards the release state,
- and from the injection position, proximally towards a safety position, in which the needle is covered by the body, along a second travel distance along which the attaching element or attaching means are in the engaged state.

Thus, owing to the invention, the patient can place the body receiving the syringe onto the skin and depress the plunger rod in one and a single movement for the whole injection process. This distal movement of the plunger rod first entails the whole syringe to move distally, insofar as the attaching element or attaching means are in the engaged state with the plunger rod. In other words, in a first phase, the needle pricks the skin while the injection has not begun. The injection cannot take place as long as the pricking is not completed. Then, in a second phase, injection can begin as the attaching element or attaching means are in a release state from the plunger rod, while the user continues the same distal movement on the plunger rod. Injection can only occur when pricking is completed, which ensures injection is carried out properly.

Finally, once injection is completed, the patient can remove his/her fingers from the plunger rod, which allows the syringe to automatically retract proximally in the body in the safety position, to avoid needle stick injury.

In practice, the coupling device is preferably configured to support the barrel.

In concrete terms, the injection position corresponds to an axial position of the coupling device relative to the body, which remains unchanged during the whole injection process, i.e. when the drug is being injected to the patient. However, the coupling device may undergo other deformations or movements than an axial movement during this injection process. Thus, in the injection position, some components of the protective assembly or injection system may move during the injection process, from the moment before injection has begun until the moment when injection is completed.

In the present application, the distal end of a piece or a device is understood to be the end furthest from the hand of the user and the proximal end is understood to be the end closest to the hand of the user. Likewise, in the present application, "distal direction" is understood to be the direction of injection, and "proximal direction" is understood to be the direction opposite the direction of injection.

The invention makes it possible to reduce the fear of accidental needle stick as the needle is covered both before use and after use, and further facilitate the injection process for patients who have difficulties to prick themselves as it can be emotionally difficult.

The attaching element or attaching means can be elastically deformable, from the engaged state to the release state, preferably by being outwardly deflectable.

The attaching element or attaching means may comprise a plunger rod engaging portion configured to cooperate with the plunger rod.

In an embodiment, such a cooperation allows the coupling device to be axially fixed with the plunger rod in an engaged state of the attaching element or attaching means, on the one hand, and the plunger rod to move the attaching element or attaching means from the engaged state to the release state, on the other hand. In other words, with such an arrangement, it is the plunger rod that moves the attaching element or attaching means towards the release state, while the attaching element or attaching means automatically move elastically back to the engaged state when injection is completed.

The plunger rod engaging portion may be a projection configured to be inserted in a cavity of the plunger rod.

The attaching element or attaching means may also comprise an elastically deformable portion. The elastically deformable portion may be the plunger rod engaging portion or another part of the coupling device, for example a lateral surface of the coupling device.

More precisely, the attaching element or attaching means preferably comprises a lateral wall that is elastically deformable and a protrusion extending inwardly from the lateral wall, the protrusion being configured to be inserted in a cavity of the plunger rod in order to axially fix together the plunger rod and the coupling device. The lateral wall is preferably cylindrical.

The body can comprise a holding element or holding means configured to maintain the attaching element or attaching means in the engaged state when the coupling device moves from the storage position to the injection position, and when the coupling device moves from the injection position to the storage position. Besides, when the coupling device no longer moves and is in the injection position, the attaching element or attaching means are on the contrary free to move to the release state.

In an embodiment, the holding element or holding means comprise a stop surface arranged radially adjacent to the attaching element or attaching means when they are in the engaged state, to prevent said attaching element or attaching means from deflecting outwardly towards the release state. The stop surface is preferably cylindrical.

The body may further include an inner recess for allowing the attaching element or attaching means to deflect outwardly towards the release state when the coupling device is in the injection position. The inner recess is preferably cylindrical.

The protective assembly can comprise a distal axial blocking element or distal axial blocking means for preventing distal movement of the coupling device relative to the body in the injection position. Maintaining the syringe and protective assembly in the injection position, even if the action on the plunger rod is released, allows the patient to momentarily stop injection whenever he/she feels the need, while ensuring the whole system remains in the position in which it was left. Consequently, the injection can be resumed without any problem, in particular without drug being lost.

The distal axial blocking element or distal axial blocking means may include a distal abutment. According to an embodiment, there may be no direct contact between the coupling device and the distal abutment. For example, a biasing element or biasing mean can be arranged between the coupling device and the distal abutment, with the biasing element or biasing mean being in its fully compressed state in the injection position, in order to prevent distal movement of the coupling device. According to another embodiment, there may be provided a lug on the coupling device and an abutting surface on the body, for example arranged in a guiding path (or the reverse configuration).

The protective assembly can further comprise a proximal abutment for preventing proximal movement of the coupling device relative to the body in the injection position, as long as the attaching element or attaching means are in the release state.

In an embodiment, the protective assembly may comprise an axial retaining element or axial retaining means for retaining the coupling device axially in the storage position. The axial retaining element or axial retaining means can comprise: a guiding path, such as a groove, in which a lug of the coupling device can move; or a tooth beyond which the coupling device can pass only if a sufficient force is exerted; or at least one wing capable of collapsing above a predetermined force exerted on the plunger rod.

The protective assembly may further comprise a biasing element or biasing means configured to bias the coupling device relative to the body proximally from the injection position towards the safety position. The biasing element or biasing means can typically be compressed in the injection position. The biasing element or biasing means preferably comprise a spring.

In an embodiment, the body comprises a proximal tooth which is configured, when in a rest position, to prevent a proximal movement of the coupling device relative to the body from the storage position, and which can be deflected to allow the coupling device to move relative to the body from the injection position towards the safety position, beyond the storage position in the proximal direction. In such a configuration, the second travel distance is greater than the first travel distance.

The protective assembly can further comprise a blocking element or blocking means of the coupling device in the safety position. For example, said blocking element or blocking means may comprise:
  a proximal abutment;
  and/or at least one safety arm protruding inwards to form a distal abutment, and outwardly deflectable by the coupling device when it moves proximally towards the safety position.

The coupling device may comprise a collar configured to support the barrel.

According to an embodiment, the coupling device comprises:
  a collar, the collar being preferably capable of rotating relative to the body about the axis;
  and/or a ring which is distinct from the collar and which is arranged proximally from said collar, the ring including the attaching element or attaching means.

The collar and the ring can be configured to be arranged on either side of a syringe flange, and not secured to said flange but maintained integral with it as regards axial movement relative to the body. For example, this can be achieved by means of a biasing element or biasing means pushing the collar, flange and ring proximally, in combination with a complementary attaching element or attaching means on the plunger rod which axially retain the attaching element or attaching means of the ring.

Alternatively, the coupling device can comprise a single part which includes a fixing element or fixing means to be axially fixedly mounted onto a syringe barrel, typically onto the flange of the syringe barrel. By "single part" is meant that, in the mounted position, the coupling device is not made of two separate parts that can move relative to one another. However, in practice, such a "single part" can result from the assembly of initially separate parts for mounting purposes.

Advantageously, the body comprises a guiding path and the collar comprises a lug engaged in the guiding path, or the reverse configuration. The guiding path preferably includes a first portion which is tilted with respect to the axis, for guiding the lug when the coupling device moves from the storage position to the injection position, and a second portion which is parallel to the axis, for guiding the lug when the coupling device moves from the injection position to the safety position.

The guiding path may further comprise a preliminary portion having the shape of a V pointing distally. An end of the V is connected to the first portion of the guiding path receiving the lug in the storage position, and the other end of the V receives the lug before removal of a cap remover initially mounted on an opened distal end of body and secured to a needle shield. The preliminary portion guides the lug during removal of the cap remover and needle shield, before use of the injection system including a syringe and the protective assembly. Such an arrangement makes it possible to avoid shocks on the syringe when the cap remover and needle shield are removed.

The body can have outwardly extending flanges configured so that a user may place two of his/her fingers under the outwardly extending flanges and one finger on the plunger rod. Owing to this feature, the pricking force is not exerted on the patient's skin, but between the plunger rod and the body, which makes injection less uncomfortable for the patient.

According to a second aspect, the invention relates to an injection system comprising a syringe, the syringe comprising a barrel, a plunger rod and a needle, the injection system further comprising a protective assembly as previously described, the barrel being supported by the coupling device.

The plunger rod may include:
a first complementary attaching element or attaching means configured to cooperate with the coupling device attaching element or attaching means when the coupling device moves from the storage position to the injection position;
and a second complementary attaching element or attaching means which are distinct from the first complementary attaching element or attaching means and located proximally from them, and which are configured to cooperate with the coupling device attaching element or attaching means when the coupling device moves from the injection position to the safety position;
wherein, for example, the first and/or complementary attaching element or attaching means comprise a cavity for receiving a plunger rod engaging portion of the attaching element or attaching means.

The cavity can be a notch or a groove, for example. According to one embodiment, the groove may be annular.

The injection system can comprise an actuating member configured to deflect the proximal tooth of the body when the coupling device moves from the injection position towards the safety position.

According to an embodiment, the actuating member is provided on the plunger rod, for example in the form of an outward protrusion having a proximal sloped surface.

According to another embodiment, the actuating member is provided on the coupling device, for example on the ring pertaining to said coupling device.

The injection system may further comprise a needle shield in which the needle is housed before use. The needle shield can include an inner soft portion in which the needle is embedded before use. The needle shield may also include an outer rigid portion at least partially surrounding the inner soft portion. The injection system may further comprise a cap remover initially mounted on the opened distal end of the body and secured to the needle shield, so that the removal of the cap remover entails the removal of the needle shield from the syringe. With such an arrangement, a preliminary portion of a guiding path may be provided on the body for guiding a lug provided on the coupling device during the removal of the cap remover, before the use of the injection system including the syringe and the protective assembly. This makes it possible to avoid shocks on the syringe when the cap remover and needle shield are removed.

According to a third aspect, the invention relates to a process for operating an injection system including a syringe, the syringe comprising a barrel, a plunger rod and a needle, the injection system further comprising a protective assembly, the barrel being supported by the coupling device, the process comprising the following steps:
placing the injection system in a storage position, with a distal end of the body in contact with an injection site;
pushing the plunger rod distally relative to the body up to the most distal position of said plunger rod, thereby causing:
in a first phase, the barrel to move distally relative to the body, while the plunger rod does not axially move relative to the barrel, to cause the needle extending beyond the body and pricking the injection site, until an injection position;
in a subsequent second phase, the plunger rod to move distally relative to the barrel, while the barrel does not axially move relative to the body, to cause injection;
releasing the plunger rod and removing the injection system from the injection site, thereby enabling both the plunger rod and the barrel to move towards a safety position in which the needle is covered by the body.

The process may further comprise a preliminary step consisting in removing a cap remover and a needle shield prior to use of the injection system.

The invention also relates to a plunger rod of a syringe, the plunger rod including:
a first complementary attaching element or attaching means;
and a second complementary attaching element or attaching means which are distinct from the first complementary attaching element or attaching means and located proximally from them;
wherein the first and second complementary attaching elements or attaching means are configured to selectively cooperate with an attaching element or attaching means of a coupling device supporting a barrel of the syringe, in order to axially fix the coupling device and the plunger rod.

According to another embodiment, the invention relates to a protective assembly for a syringe including a barrel, a plunger rod and a needle. The protective assembly includes an axis, a body for receiving the syringe and extending along the axis, and a coupling device arranged inside the body. The coupling device is configured to be rigidly connected to the barrel as regards to axial movement relative to the body. The coupling device includes an attaching element configured to be either in an engaged state with the plunger rod in order to axially fix the coupling device and the plunger rod, or in a release state in which the coupling device and the plunger rod are axially free relative to one another. The coupling device is axially movable in the body from a storage position, distally along a first travel distance along which the attaching element is in the engaged state, to an injection position in which the needle extends beyond the body, and in which the attaching element is free to move towards the release state. The coupling device is axially movable in the body from the injection position, proximally towards a safety position, in which the needle is covered by the body, along a second travel distance along which the attaching element is in the engaged state.

According to another embodiment, the invention relates to an injection system including a syringe including a barrel, a plunger rod and a needle; and a protective assembly. The protective assembly includes an axis, a body for receiving the syringe and extending along the axis, and a coupling device arranged inside the body. The coupling device is configured to be rigidly connected to the barrel as regards to axial movement relative to the body. The coupling device includes an attaching element configured to be either in an engaged state with the plunger rod in order to axially fix the coupling device and the plunger rod, or in a release state in which the coupling device and the plunger rod are axially free relative to one another. The coupling device is axially movable in the body from a storage position, distally along a first travel distance along which the attaching element is in the engaged state, to an injection position in which the needle extends beyond the body, and in which the attaching element is free to move towards the release state. The coupling device is axially movable in the body from the injection position, proximally towards a safety position, in which the needle is covered by the body, along a second travel distance along which the attaching element is in the engaged state. The barrel of the syringe is supported by the coupling device of the protective assembly.

According to another embodiment, the invention relates to a process for operating an injection system including a syringe including a barrel, a plunger rod and a needle; a protective assembly, the barrel being supported by a coupling device of the protective assembly. The process includes placing the injection system in a storage position, with a distal end of the body in contact with an injection site. The process further includes pushing the plunger rod distally relative to the body up to the most distal position of said plunger rod, thereby causing: in a first phase, the barrel to move distally relative to the body, while the plunger rod does not axially move relative to the barrel, to cause the needle extending beyond the body and pricking the injection site, until an injection position; and in a subsequent second phase, the plunger rod to move distally relative to the barrel, while the barrel does not axially move relative to the body, to cause injection. The process further includes releasing the plunger rod and removing the injection system from the injection site, thereby enabling both the plunger rod and the barrel to move towards a safety position in which the needle is covered by the body.

BRIEF DESCRIPTION OF THE DRAWINGS

A possible embodiment of the invention will now be described by way of non-limiting examples with reference to the appended figures:

FIG. 5 is a perspective exploded view of an injection system according to another embodiment of the invention;

FIG. 6 is a top view of the injection system of FIG. 5;

FIGS. 7a-7d show the injection system equipped with a cap remover, before use, respectively in cross section along line AA of FIG. 6, in cross section along line BB of FIG. 6, and in detail around the coupling device according to two different viewing directions;

FIGS. 11a-11d show the injection system after pricking, in the injection position, before injection begins, respectively in cross section along line AA of FIG. 6, in cross section along line BB of FIG. 6, and in detail around the coupling device according to two different viewing directions;

FIGS. 13a-13e show the injection system in the safety position, respectively in cross section along line AA of FIG. 6, in cross section along line BB of FIG. 6, and in detail around the coupling device according to three different viewing directions;

DESCRIPTION OF THE INVENTION

Figure 1:
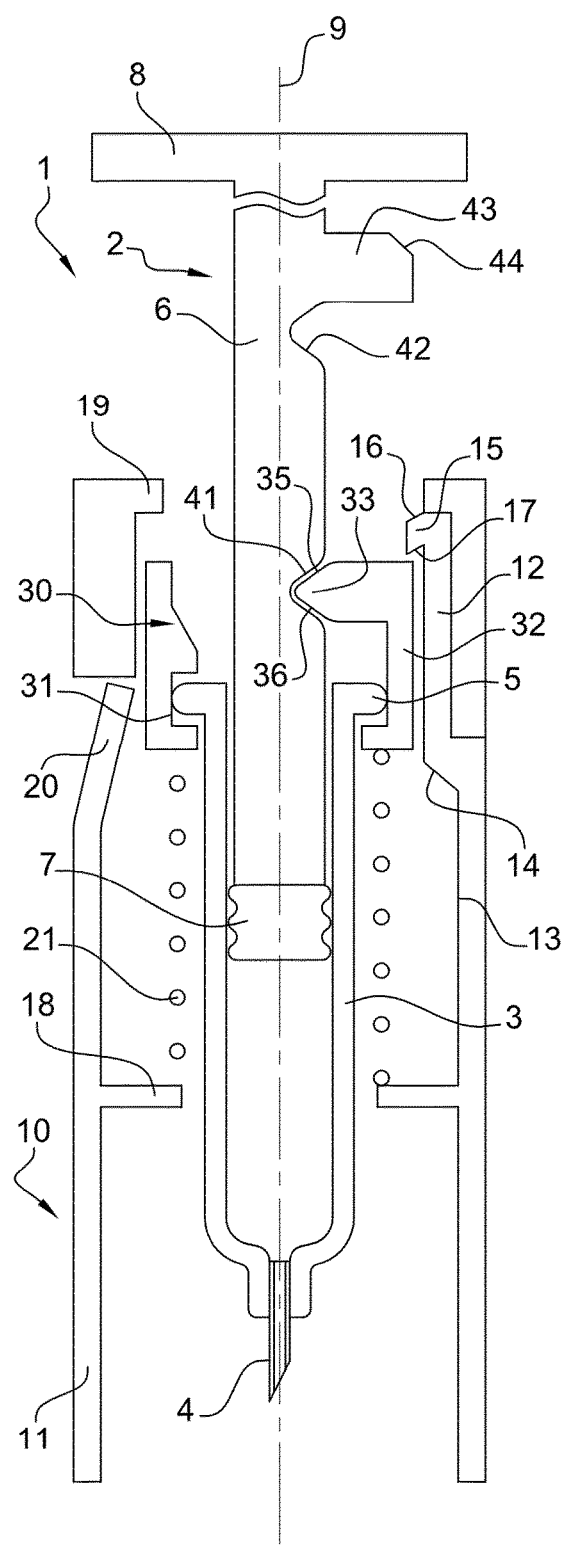
FIG. 1 is a schematic cross-section view in two orthogonal planes of an injection system according to an embodiment of the invention, in the storage position.
Figure 2:
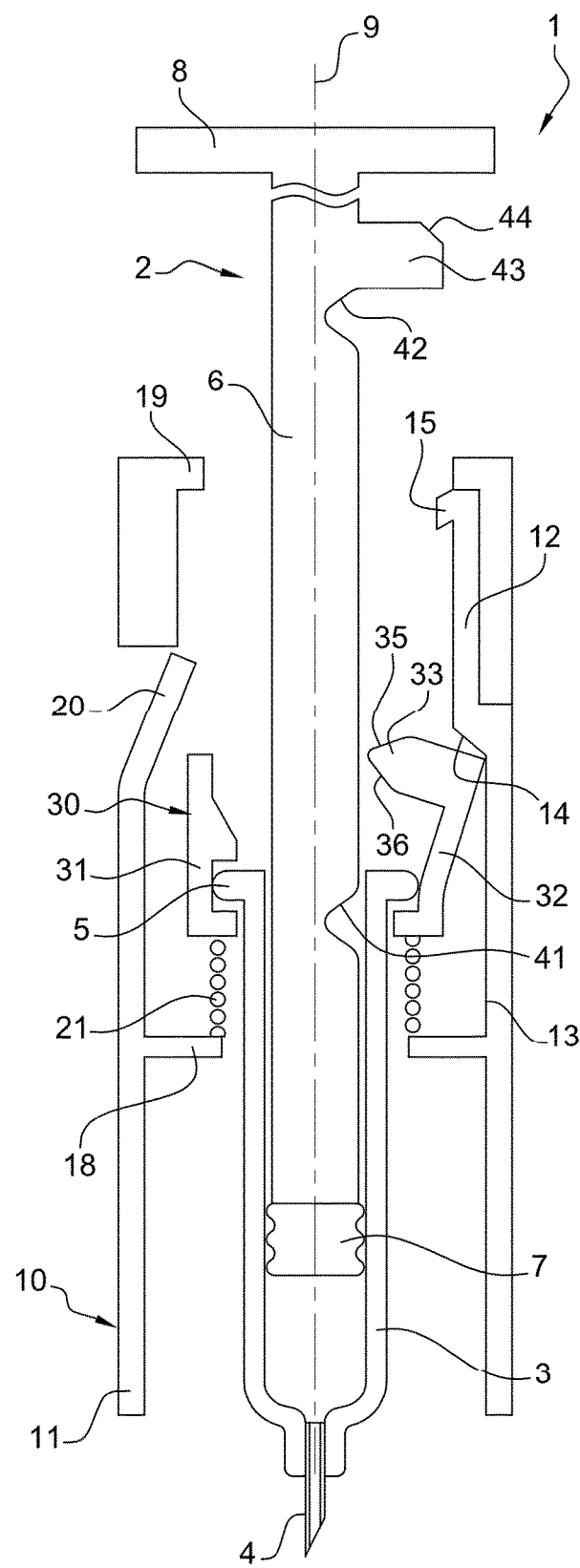
FIGS. 2, 3 and 4 are cross-section views of the injection system of FIG. 1, in two orthogonal planes, respectively in the injection position before the injection has started, in the injection position when the injection is completed, and in the safety position.

The invention relates to an injection system 1 which comprises a syringe 2 and a protective assembly 10 especially designed for preventing needle stick injuries.

The syringe 2 comprises a barrel 3 designed to contain a drug to be injected to a patient. The barrel 3 has a distal end equipped with a needle 4, and a proximal end including a flange 5 that can typically protrude radially outwardly. A plunger rod 6 is inserted in the barrel 3 for expelling the drug distally through the needle 4. The plunger rod 6 includes a distal stopper 7 and a proximal member 8, typically disc-shaped, to allow a user to push the plunger rod 6 distally.

The protective assembly 10 basically comprises a body 11 which receives the syringe 2, and a coupling device 30 arranged inside the body 11.

In use, the injection system 1, syringe 2 and protective assembly 10 have a common axis 9.

The body 11 is preferably cylindrical. The body 11 comprises:
- a proximal portion 12, which is preferably cylindrical;
- an inner recess 13 having a greater inner diameter than the proximal portion 12. The inner recess 13 is preferably cylindrical. The inner recess 13 can be proximally delimited by a proximal face 14 joining the proximal portion 12 and the inner recess 13. The proximal face 14 is preferably angled.

The body 11 can further comprise a distal abutment 18 configured to axially stop the coupling device 30.

A tooth 15 extending inwardly can be provided near the proximal end or at the proximal end of the body 11. The tooth 15 is preferably flexible so that the coupling device may 30 may cross it when it is pushed with a force higher than a predetermined force. The tooth 15 can have a sloped proximal face 16 and a blocking distal face 17, for example extending radially.

An inwardly extending organ may be provided at the proximal end of the body 11, forming a proximal abutment 19. Besides, the body 11 may comprise at least one safety arm 20 located between the proximal abutment 19 and the distal abutment 18. In an embodiment, the safety arm 20 protrudes inwards at rest, and is outwardly deflectable.

Moreover, a biasing element or biasing mean 21, such as a spring, is configured to bias the coupling device 30 proximally relative to the body 11. The spring is preferably helical. The spring is preferably arranged around the barrel 3. The spring is preferably inside the body 11. The biasing element or biasing means 21 are preferably located axially between the coupling device 30 and the distal abutment 18.

The coupling device 30 is axially movable in the body 11. The coupling device 30 is configured to be rigidly connected to the barrel 3 as regards axial movement relative to the body 11.

The injection system 1 is configured to be operated easily and safely by a patient. Most precisely, the patient can hold the system the same way during the whole process and exert a single movement, namely a distal pressure on the plunger rod, to perform the whole process, including pricking and injection. This enhances stability and control. The injection system 1 is designed to ensure that pricking will happen first, and only when pricking is completed, injection can begin. The body 11 is designed to be easily positioned orthogonally to the skin.

In concrete terms, the general operation of the injection system 1 is as follows. The patient places the injection system 1 on the skin—the injection system being in a storage position, ready to use—and then pushes the plunger rod distally relative to the body. This causes:

- in a first phase, the barrel 3 to move distally relative to the body 11, while the plunger rod 6 does not axially move relative to the barrel 3, to cause the needle 4 extending beyond the body 11 and pricking the injection site, until an injection position;
- in a subsequent second phase, the plunger rod 6 to move distally relative to the barrel 3, while the barrel 3 does not axially move relative to the body 11, to cause injection.

When the plunger rod 6 has been pushed up to its most distal position, the patient can remove the injection system 1 from the skin and remove his/her fingers from the plunger rod 6, thereby enabling both the plunger rod 6 and the barrel 3 to move towards a safety position in which the needle 4 is covered by the body 11.

So that the injection system 1 can be operated as described above, the coupling device 30 comprises an attaching element or attaching means 32 having a plunger rod engaging portion 33 designed to cooperate with the plunger rod 6.

More specifically, the attaching element or attaching means 32 can be in an engaged state with the plunger rod 6, in order to axially fix the coupling device 30 and the plunger rod 6. To that end, the plunger rod engaging portion 33 can cooperate either with a first complementary attaching element or attaching means 41 of the plunger rod 6, or with a second complementary attaching element or attaching means 42 of the plunger rod 6, which are distinct from the first complementary attaching element or attaching means 41 and located proximally from them. In practice, the plunger rod engaging portion 33 can be a projection 33, i.e. a portion protruding towards the plunger rod 6, and the complementary attaching elements or attaching means 41, 42 can be a cavity for receiving the portion 33. The projection 33 preferably comprises a proximal surface 35 which is angled, and/or a distal surface 36 which is angled. The cavity and projection 33 can have corresponding shapes. In such an engaged state, the attaching element or attaching means 32 can be in a rest position. The attaching element or attaching means 32 can be maintained in an engaged state with the plunger rod 6 by means of the proximal portion 12 of the body 11, which prevents outward movements of the coupling device 30.

Besides, from the engaged state, the attaching element or attaching means 32 can move, for example by elastic outward deformation, to a release state, in which the coupling device 30 and the plunger rod 6 are axially free relative to one another. This movement from the engaged state to the release state can result from the cooperation between the projection 33 of the attaching element or attaching means 32 and the plunger rod 6. This movement is possible when the coupling device 30 no longer faces the proximal portion 12 of the body 11, but is facing the inner recess 13.

More precisely, in an embodiment, the attaching element or attaching means 32 may comprise:

- an elastically deformable portion, such as an elastically deformable, preferably cylindrical, lateral wall;
- and a projection 33 extending inwardly from the lateral wall. The projection 33 is configured to be inserted in a cavity 41, 42 of the plunger rod 6 in order to axially fix together the plunger rod 6 and the coupling device 30.

Reference is now made to FIGS. 1 to 4 which show a first embodiment of the invention. It has to be noted that, in each of these figures, the left half in a cross section view of the injection system 1 in a first longitudinal plane, while the right half in a cross section view of the injection system 1 in a second longitudinal plane that is orthogonal to the first plane.

In this embodiment, the coupling device 30 is made of a single part. However, it could be made of several parts. The barrel 3 is supported on the coupling device 30. The coupling device 30 can be fixedly mounted relative to the barrel 3, typically onto the flange 5, owing to a fixing element or fixing means 31. The fixing element or fixing means 31 can comprise an annular groove into which the flange 5 is received.

In a storage position, illustrated in FIG. 1, the attaching element or attaching means 32 are in the engaged state, with the projection 33 engaged in the first complementary attaching element or attaching means 41 of the plunger rod 6. The spring 21 is partially compressed and pushes the coupling device 30—and thus barrel 3 and plunger rod 6—proximally. The proximal tooth 15 is in a rest position and prevents a proximal movement of the coupling device 30 and syringe 2 relative to the body 11. The needle 4 is covered by the body 11 of the protective assembly 10.

When the plunger rod 6 is pushed distally, it entails the same distal movement of the coupling device 30 since the coupling device 30 and the plunger rod 6 are axially fixed thanks to the projection 33 engaged in the first complementary attaching element or attaching means 41. Therefore, owing to the fixing element or fixing means 31, the barrel 3 is also moved distally together with the plunger rod 6. This causes the needle 4 to move beyond the body distal end and prick the patient's skin, with the pricking effort not being exerted on the patient's skin, but between the plunger rod 6 and the body 11, as previously explained, owing to the outwardly extending flanges. During this first phase of the movement, the proximal portion 12 of body 11 forms a holding element or holding means which maintains the attaching element or attaching means 32 in the engaged state, therefore ensuring the plunger rod 6 cannot move relative to the barrel, i.e. injection cannot begin.

During this movement, the spring 21 is progressively compressed. It can for example reach its fully compressed state, though this is not limitative.

Once pricking is completed, the injection system 1 is in the injection position. The coupling device 30 then enters the inner recess 13. The coupling device 30 is axially distally blocked, preferably by spring 21 compressed against distal abutment 18, or any other axial distal abutment. As a consequence, when the plunger rod 6 is pushed further distally, the projection 33 is caused to disengage out of the first complementary attaching element or attaching means 41, with the attaching element or attaching means 32 being outwardly deformed. This outward movement is possible as the coupling device 30 is now facing the recess 13 and not the proximal portion 12 of body 11 any more. In this position, illustrated in FIG. 2, injection can begin.

It has to be noted that, in the injection position, the coupling device 30 is preferably located distally from the safety arm 20. Consequently, the safety arm 20 is free to protrude inwards.

The patient goes on pushing the plunger rod 6 distally. As the barrel 3 cannot move further distally and the attaching element or attaching means 31 are in the released state, this causes the plunger rod 6 to move distally inside the barrel 3, i.e. the drug to be injected. As the coupling device 30 is axially maintained, in this example by the spring 21 and distal abutment 18, on the one hand, and by the proximal face 14 of the recess 13, on the other hand, the patient can release the plunger rod 6 without said plunger rod to move. Injection can then be resumed without any problem.

Figure 3:
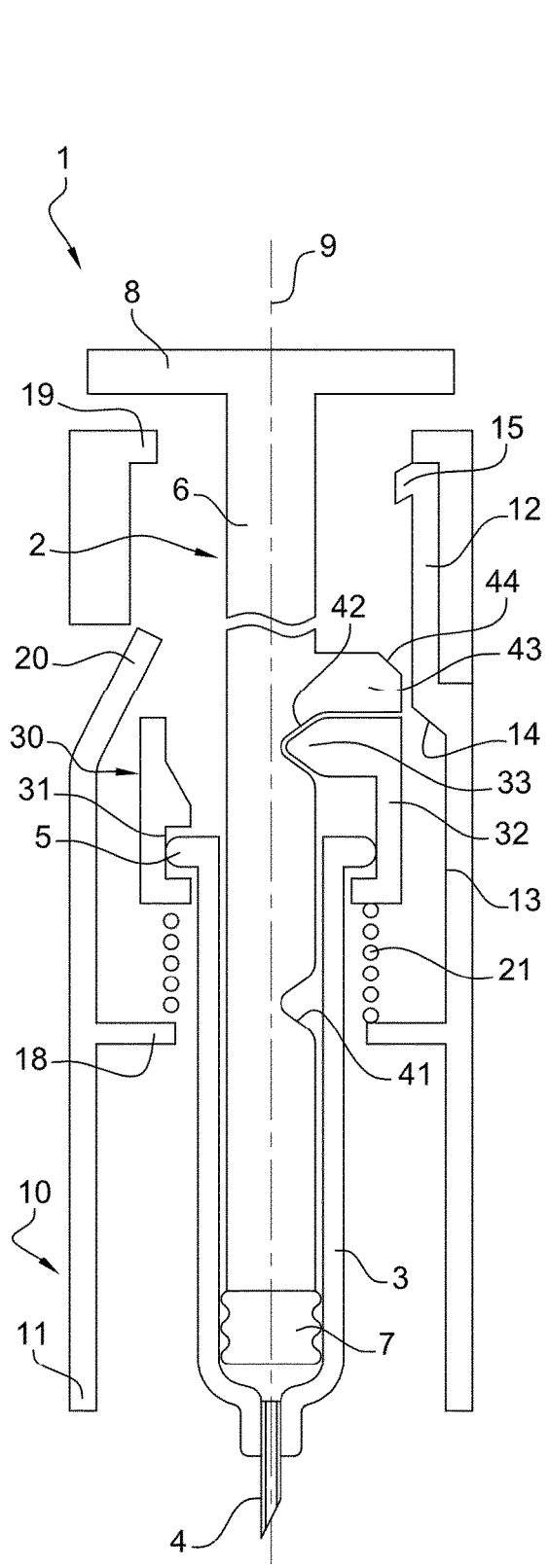

At the end of injection, as shown in FIG. 3, the projection 33 faces the second complementary attaching element or attaching means 42 of the plunger rod 6 and engages in it by elastic movement back to its engaged state. The coupling device 30 is thus again axially fixed to the plunger rod 6.

Figure 4:
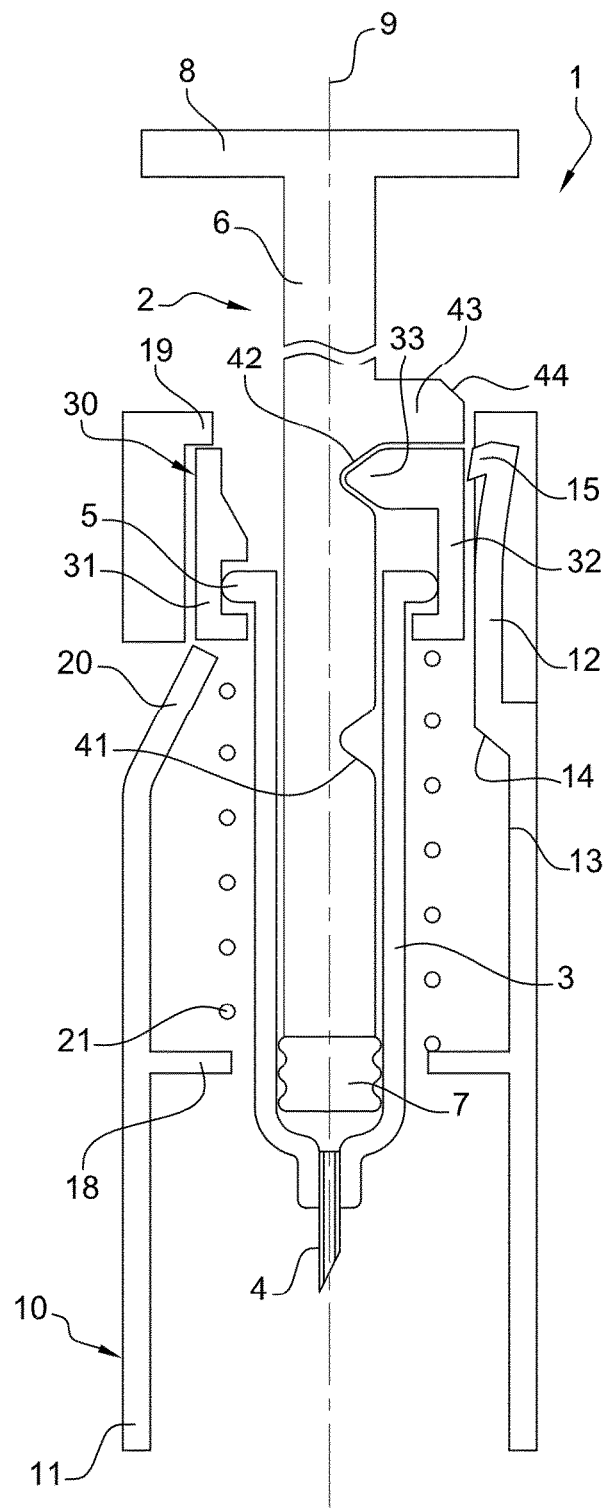

When the patient removes the injection system 1 from the injection site and his/her fingers from the plunger rod 6, the force of the spring 21 causes the coupling device 30, barrel 3 and plunger rod 6, as a whole, to move proximally towards a safety position, illustrated in FIG. 4, in which the needle 4 is covered by the body 11 of the protective assembly 10. The coupling device 30 remains axially fixed to the plunger rod 6 due to the proximal portion 12 of body 11 which maintains the attaching element or attaching means 32 in the engaged state.

During this movement, the coupling device 30 has deflected the safety arm 20 outwardly and has moved further distally, thereby allowing said safety arm 20 to move elastically back to its rest position in which it protrudes inwards.

Furthermore, the proximal tooth 15 of the body 11 has been deflected outwardly by an actuating member provided on the plunger rod 6, to allow the syringe 2 to move proximally beyond the storage position. The actuating member can be an outward protrusion 43 having a proximal sloped surface 44 for cooperating with the blocking proximal face 17 of the tooth 15.

The coupling device 30 and the syringe 2 are maintained in the safety position relative to the body 11 by means of the proximal abutment 19 and the safety arm 20, ensuring the needle 4 will remain covered by the body 11.

Reference is now made to FIGS. 5 to 13e which show a second embodiment of the invention.

The protective assembly comprises a body 11 comprising a proximal portion 12 configured to maintain the attaching element or attaching means 32 in the engaged state and an inner recess 13 having a greater inner diameter than the proximal portion 12 in which the attaching element or attaching means 32 are free to move towards the release state. The inner recess 13 is located distally from the proximal portion 12.

In this embodiment, as shown in FIG. 5, the body 11 may be made of a distal portion 50 and two halves 51, 52 forming a proximal portion, which are assembled, for example snapped together. Moreover, the proximal open end of the body 11 is closed by a plug 53 which slidably receives the plunger rod 6. Alternatively, the body 11 may be made of a single piece.

The body 11 can have outwardly extending flanges 60 on which a user can place his/her fingers, so that the injection force is exerted between the plunger rod 6 and the body 11.

The injection system 1 may also comprise a needle shield 54 including an inner soft portion 55 in which the needle 4 is embedded before use. The needle shield may also comprise an outer rigid portion 56 (see FIGS. 7a and 7b).

In the illustrated embodiment, the injection system 1 further comprises a cap remover 57 configured to remove the needle shield 54 from the needle. The cap remover 57 may be initially mounted on the opened distal end of the body 11 and secured to the needle shield 54, for example by means of attaching arms 58. The cap remover 57 is thus removably mounted on the syringe distal end.

The protective assembly comprises a coupling device 30 comprising the attaching element or attaching means 32 configured to support the barrel 3. The coupling device 30 comprises the attaching element or attaching means 32 which are configured to be either in an engaged state with the plunger rod 6 in order to axially fix the coupling device 30 and the plunger rod 6, or in a release state in which the coupling device 30 and the plunger rod 6 are axially free relative to one another.

According to this embodiment, the coupling device 30 is made of two separate parts, namely a collar 61 and a ring 62. The collar 61 is arranged distally from the barrel flange 5, and the ring 62 is arranged proximally from said flange 5. A washer 63 may be further provided around the barrel 3, distally from the collar 61, to avoid friction—in particular rotational friction—between the collar 61 and the spring 21.

The spring 21 pushes the washer 63 when it is present, and the collar 61 proximally against the flange 5, and the flange 5 proximally against the ring 62. Therefore, the ring 62 and collar 61—which together form the coupling device 30—can be rigidly connected to the barrel 3 as regards axial movement relative to the body 11, even if the coupling device 30 is not axially secured to the barrel 3.

The collar 61 is preferably capable of rotating relative to the body 11 about the axis 9. It comprises a lug 64 which protrudes outwardly and which preferably has a tapered shape forming a proximal tip. The ring 62 includes the attaching element or attaching means 32. More precisely, the ring 62 can include two jaws 65 separated by a space 66 or slot, which can elastically move apart from one another, from the engaged state to the release state.

Besides, the body 11 comprises a guiding path 70. The guiding path 70 may be a through opening. The lug 64 of the collar 61 is engaged in the guiding path 70. As shown in FIG. 7a, for example, the guiding path 70 comprises:

an optional preliminary portion 75 having the shape of a V pointing distally. The preliminary portion comprises a first branch 71 extending from an end 73 of the guiding path 70 to the tip 76 of the preliminary portion 75, and a second branch 72 extending from the tip 76 of the preliminary portion 75 to a point 77;

a first portion 81 which extends distally from the point 77 to a point 83, and which is tilted with respect to the axis 9;

a second portion 82 which extends proximally from the point 83 to a point 84, and which is parallel to the axis 9. Point 84 can be the other end of the guiding path 70.

In an embodiment, there are provided two identical guiding paths 70 on the body, arranged opposite with respect to axis 9, each guiding path 70 receiving one lug 64 among two opposite lugs 64 provided on the collar 61.

The operation of the injection system 1 according to this second embodiment will now be described.

Figure 7C:
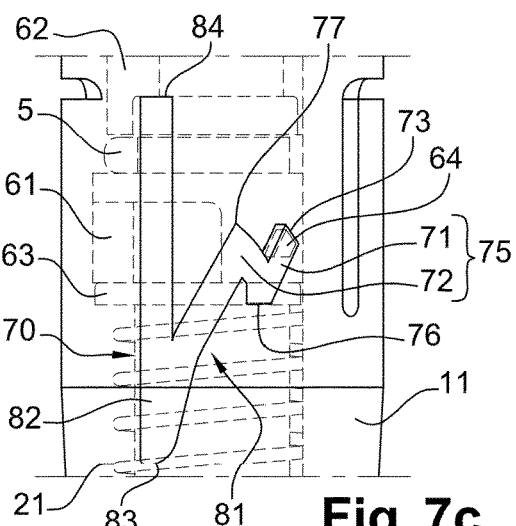

Initially, as illustrated in FIGS. 7a-7d, the attaching element or attaching means 32 are in the engaged state, with the projection 33 engaged in the first complementary attaching element or attaching means 41 of the plunger rod 6. The spring 21, which rests on a shoulder of the body 11 forming the distal abutment 18, can be partially compressed. It pushes the washer 63, collar 61, flange 5 and ring 62 axially proximally, with the ring 62 abutting against the proximal tooth 15 which is in the rest position. No further proximal movement is thus possible in this position. The needle 4 is covered by the body 11 of the protective assembly 10. The lug 64 of the collar 61 is located near the end 73 of the guiding path 70, as shown in FIG. 7c.

In case the injection system 1 is provided with a cap remover 57 before use, as previously described, a preliminary step to be performed is to remove the cap remover 57, which entails the needle shield 54 to be removed from the syringe 2.

To that end, the patient pulls the cap remover 57 distally, which causes the needle shield 54 to be also pulled distally owing to the attaching arms 58. The needle shield 54 tends to pull distally the syringe 2, causing the collar 61 to also move distally.

Figure 8A:
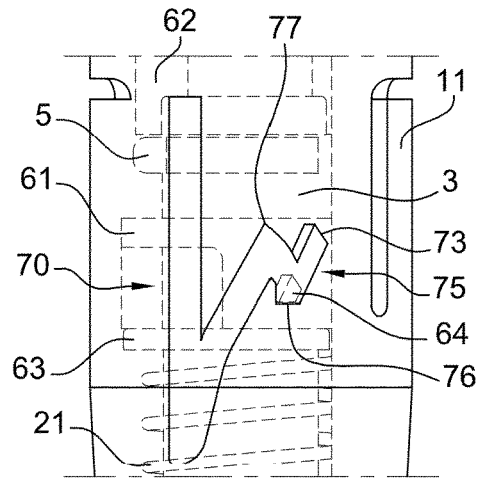
FIGS. 8a and 8b are views similar to FIGS. 7a and 7b, during the removal of the cap remover.
Figure 7D:
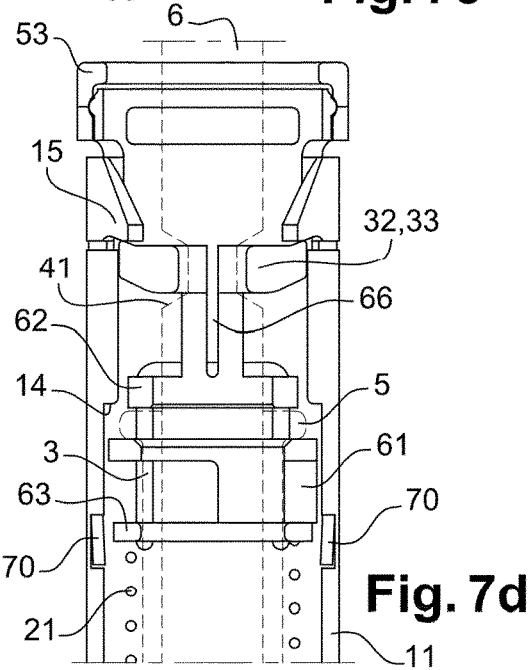
Figure 8B:
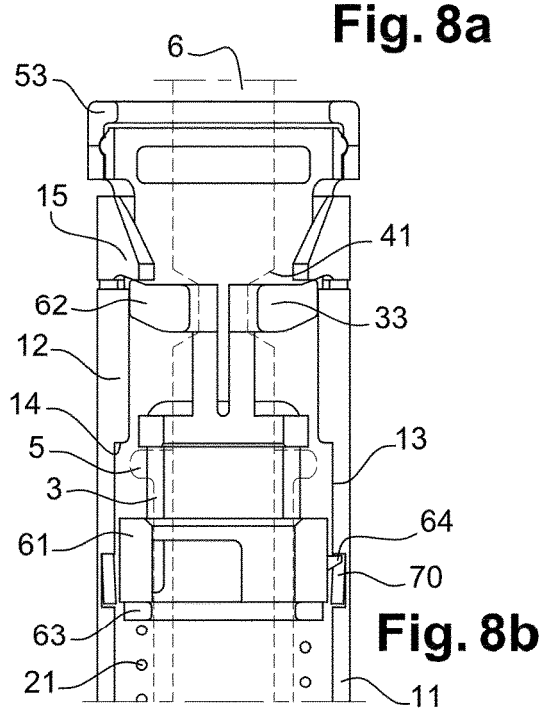

The lug 64 of the collar 61 is made to move in the preliminary portion 75 of the guiding path 70, and forces the collar 61 to rotate. During the removal of the cap remover 57, the lug 64 moves in the first branch 71 of the preliminary portion 75, from the end 73. When the lug 64 reaches the tip 76, as illustrated in FIGS. 8a and 8b, no further distal movement is possible, and the cap remover 57, together with the needle shield 54, can be removed. Owing to these features, the syringe 2 is prevented from moving proximally during the needle shield removal, which could cause the syringe 2 to be broken or damaged. These features thus allow the syringe 2 to be axially fixed relative to the body 11 as the needle shield 54 is being removed.

The protective assembly 10 may comprise an axial retaining element or axial retaining means for retaining the coupling device 30 axially in the storage position.

Figure 13E:
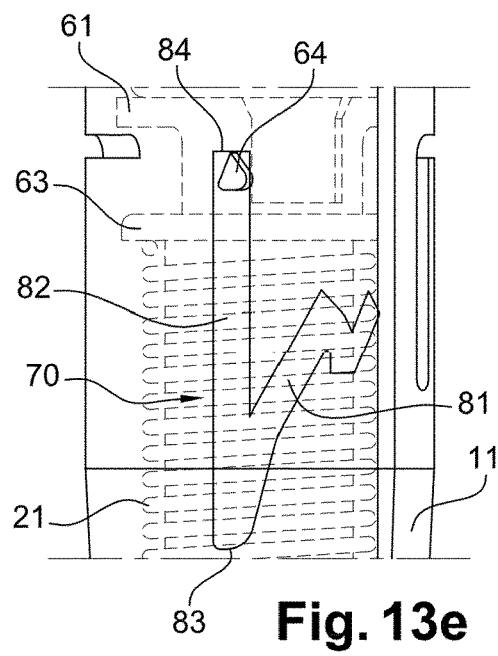
Figure 13A:
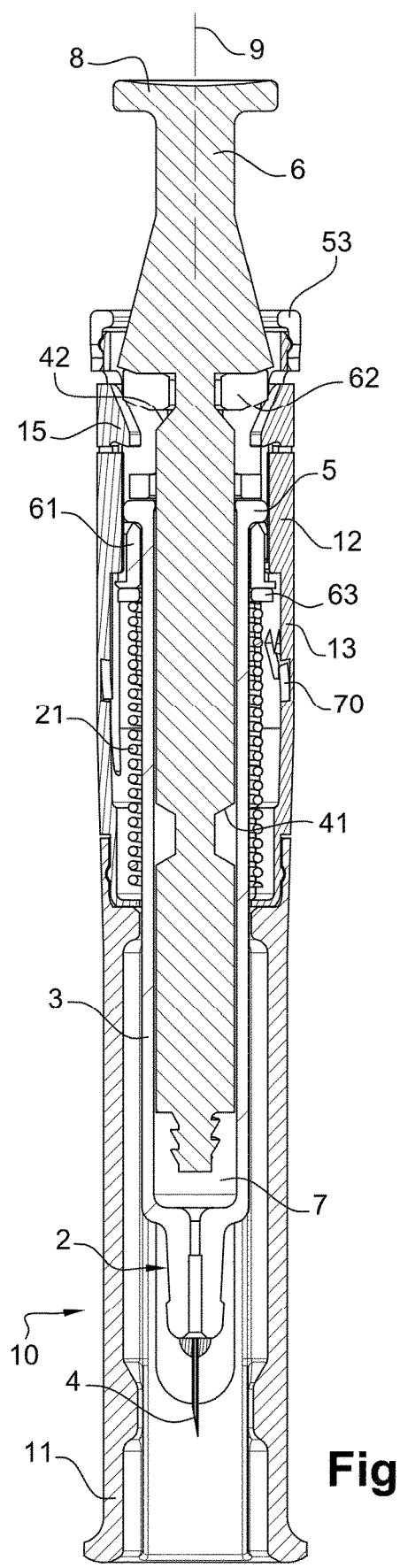
Figure 13B:
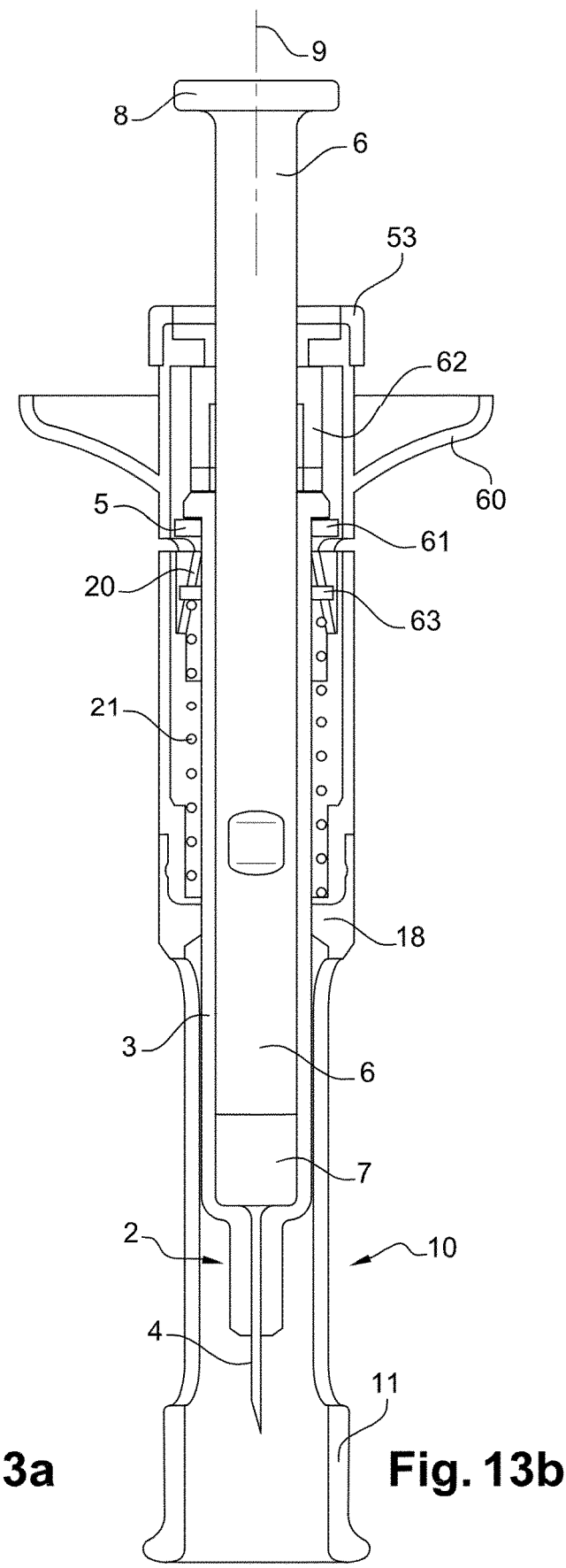
Figure 14:
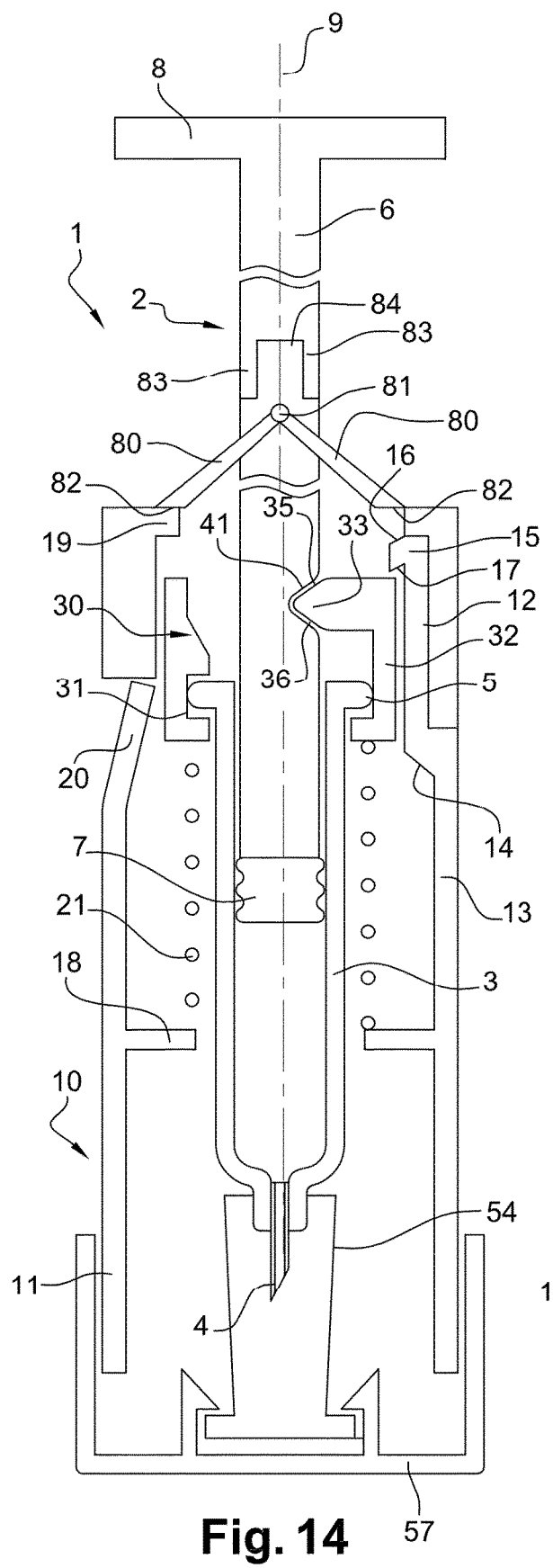
FIGS. 14 and 15 schematically and partially show an injection system comprising means for axially retaining the coupling device in the storage position, respectively in a retaining position, and when collapsed.
Figure 15:
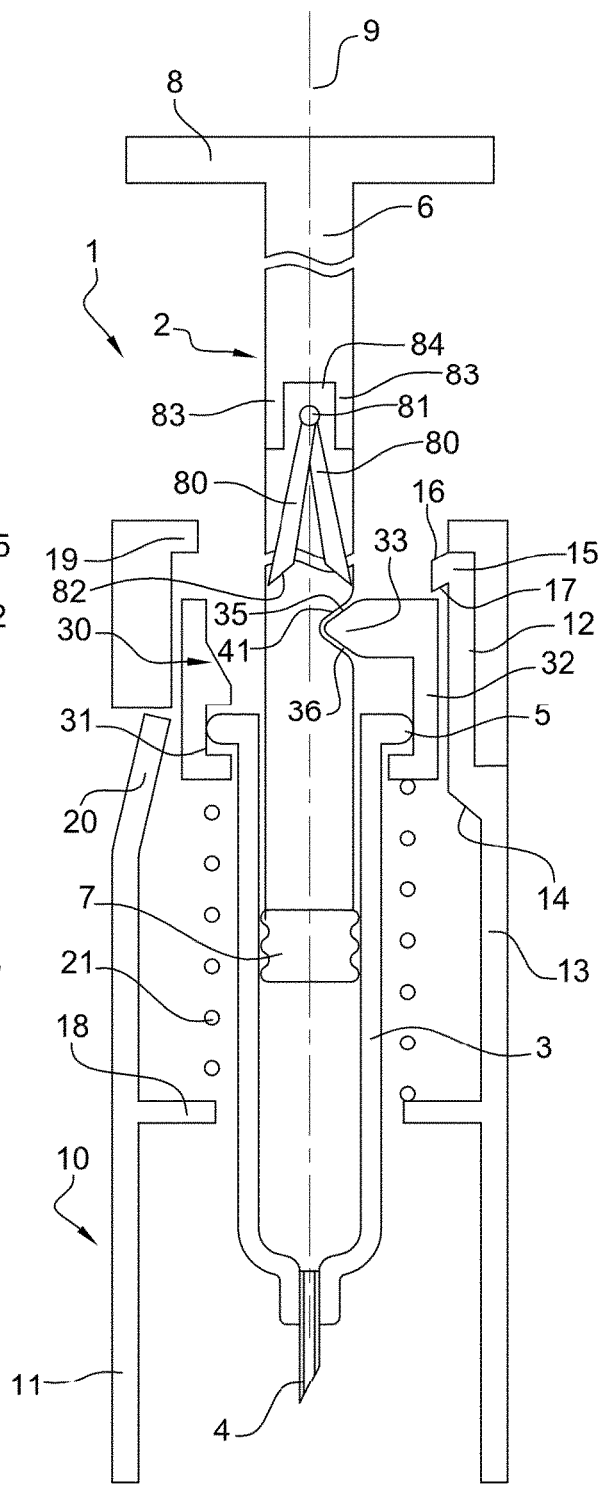

An exemplary embodiment of such axial retaining element or axial retaining means is illustrated in FIGS. 14 and 15. It has to be noted that these figures are schematic and only partially show the protective assembly. In particular, the second complementary attaching element or attaching means 42 nor the actuating member 43 are illustrated. Besides, although the protective assembly is similar to the one of FIGS. 1-4, the axial retaining element or axial retaining means could be implemented on a protective assembly similar to the one of FIGS. 5-13e.

As shown in FIG. 14, the axial retaining element or axial retaining means may comprise at least one wing 80 mounted on the plunger rod 6, for example two wings 80 arranged according to a V pointing distally. The wings 80 may have a distal end 82 abutting the body 11, for example abutting the proximal abutment 19, in the storage position. The wings 80 may further have a proximal end connected to the plunger rod 6, preferably pivotally about an axis 81 orthogonal to axis 9. Thus, the wings 80 prevent axial movement of the coupling device 30.

When a sufficient force is exerted distally on the plunger rod 6, for example during removal of a cap remover 57 coupled to a needle shield 54, the wings 80 may collapse, preferably by pivoting about axis 81. This can be caused by an appropriate actuator arranged on the plunger rod 6, such as actuating legs 83, each leg 83 pushing one wing 80. The legs 83 can delimit a cavity 84 opening distally, and capable of receiving part of the wings 80 once collapsed, i.e. when they are folded towards one another, as shown in FIG. 15.

Figure 9:
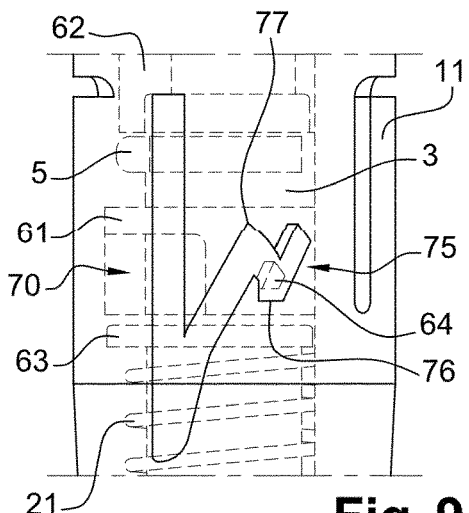
FIG. 9 is a view similar to FIG. 8a during a subsequent step of the removal of the cap remover.

When the cap remover 57 and needle shield 54 have been removed, as no distal pulling effort is exerted any more, the spring 21 pushes the washer 63 and collar 61 proximally, back to the initial position, until the collar 61 is in contact with the flange 5 of the barrel 3. During this movement, the lug 64 moves in the second branch 72 of the preliminary portion 75, from the tip 76, to the point 77. As shown in FIG. 9, the lug tapered shape and the geometry of the preliminary portion 75 ensure that the lug 64 cannot move back to the end 73, but will move towards the point 77.

When the cap remover 57 has been removed, the injection system 1 is in the storage position, ready for use.

It has to be noted that the injection system 1 is not necessarily provided with a cap remover, and that the above described steps are thus optional, as is the preliminary portion 75 of the guiding path 70.

Figure 10A:
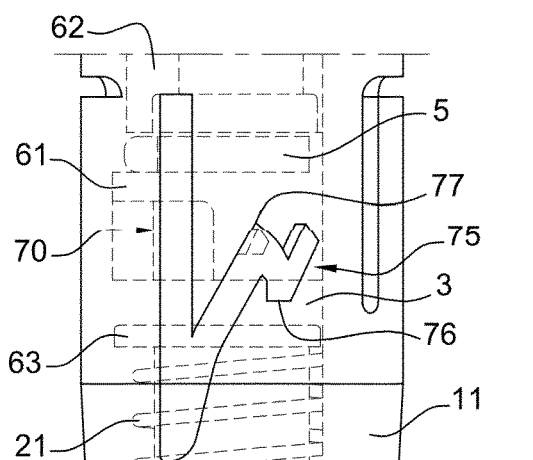
FIGS. 10a and 10b show the injection system in the storage position, after the cap remover has been removed, respectively according to a detailed view similar to FIG. 9, and in cross section along line AA of FIG. 6.
Figure 10B:
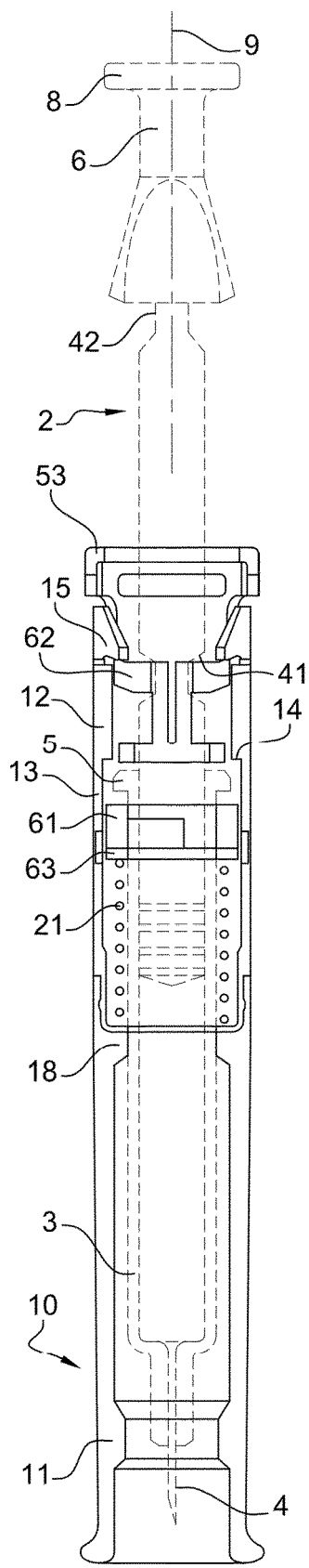

From the storage position illustrated in FIGS. 10a and 10b, the injection process can begin.

To that end, the patient pushes the plunger rod 6 distally. As the projection 33 of the attaching element or attaching means 32 of ring 62 is engaged in the first complementary attaching element or attaching means 41 of the plunger rod 6, the distal movement of the plunger rod 6 entails the same distal movement of the ring 62. This consequently causes the same distal movement of the flange 5 of barrel 3, the collar 61 and the washer 63.

In other words, the barrel 3 is moved distally together with the plunger rod 6. This causes the needle 4 to move beyond the body distal end and prick the patient's skin. During this first phase of the movement, the proximal portion 12 of body 11 forms a holding element or holding means which maintains the attaching element or attaching means 32 in the engaged state, i.e. which prevents the jaws 65 from moving apart from one another. This ensures the plunger rod 6 cannot move relative to the barrel, i.e. injection cannot begin. During pricking, the spring 21 is progressively compressed between the washer 63 and the distal abutment 18.

During this common distal movement of the plunger rod 6 and barrel 3, from the storage position to the injection position, the lug 64 of the collar 61 moves in the first portion 81 of the guiding path 70 of the body 11, until it reaches the point 83. Therefore, the coupling device 30 is axially distally blocked. Then, pricking is completed, and the injection system 1 is in the injection position.

As the coupling device 30 is axially distally blocked, when the plunger rod 6 is pushed further distally, the projection 33 is caused to disengage out of the first complementary attaching element or attaching means 41, with the attaching element or attaching means 32 being outwardly deformed. This outward movement is possible as the coupling device 30 is now facing the inner recess 13 and not the proximal portion 12 of body 11 any more. In this position, illustrated in FIGS. 11a-11d, injection can begin.

Figure 11A:
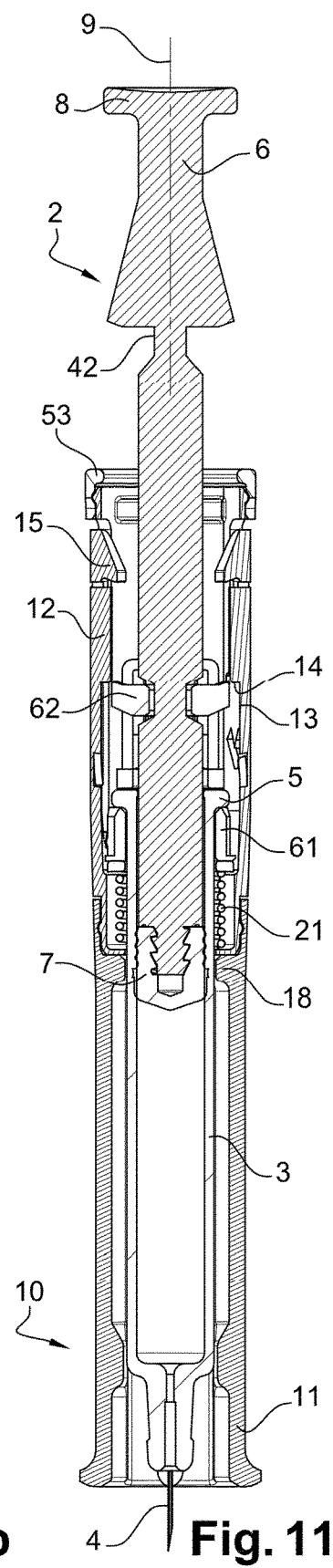
Figure 11B:
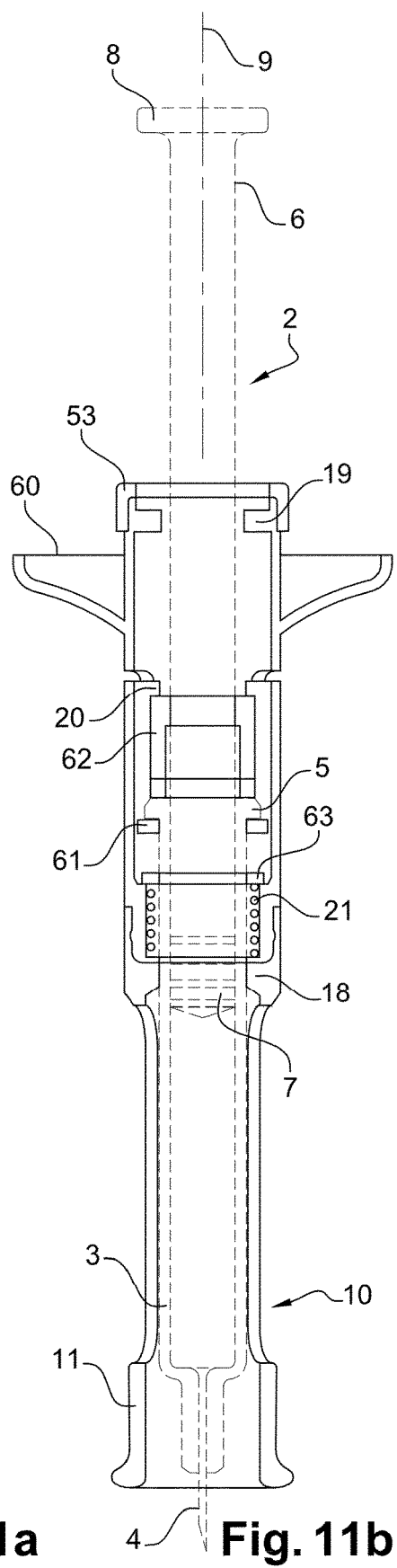

It has to be noted that, in the injection position, the coupling device 30 is preferably located distally from the safety arm 20. Consequently, the safety arm 20 is free to protrude inwards, as shown in FIG. 11b.

As the patient goes on pushing the plunger rod 6 distally, because the attaching element or attaching means 31 are in the released state, the plunger rod 6 is caused to move distally inside the barrel 3, i.e. the drug to be injected. Indeed, because the lug 64 is abutting on the point 83 of the guiding path 70, the collar 61 is distally axially blocked and, consequently, the barrel 3 cannot move distally either relative to the body 11.

The assembly comprising the collar 61, flange 5 and ring 62 is axially maintained by the lug 64, on the one hand, and by the proximal face 14 of the recess 13, on the other hand, the patient can release the plunger rod 6 without said plunger rod to move. Injection can then be resumed without any problem.

Figure 12A:
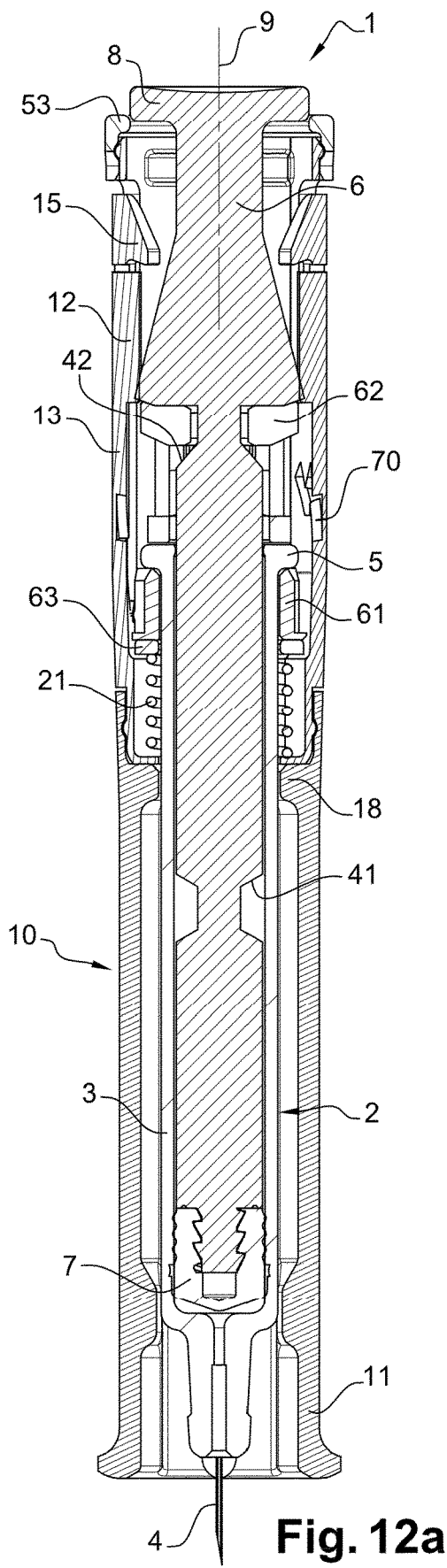
FIGS. 12a and 12b show the injection system in the injection position, when injection is completed, respectively in cross section along line AA of FIG. 6, and in detail around the coupling device.
Figure 12B:
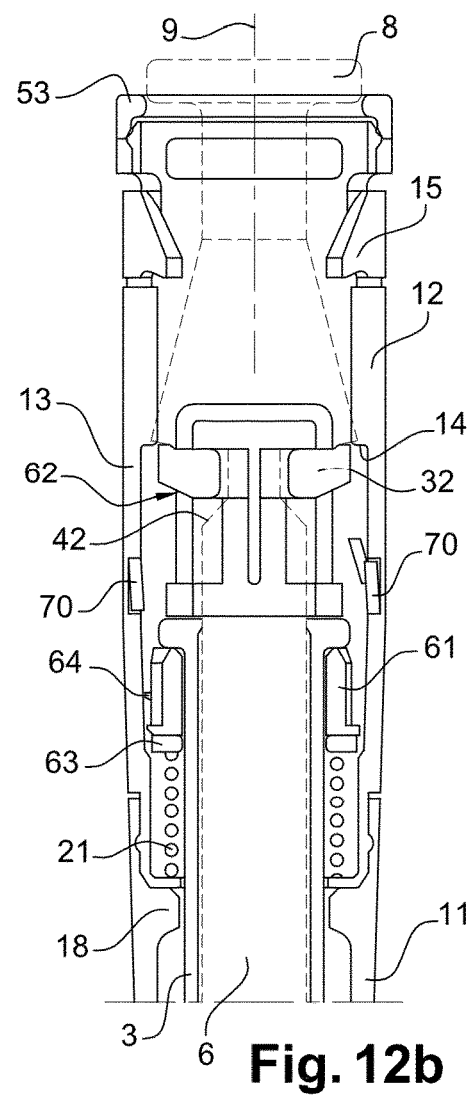

At the end of injection, as shown in FIGS. 12a and 12b, the projections 33 of the jaws 65 of the ring 62 face the second complementary attaching element or attaching means 42 of the plunger rod 6 and engage in it by elastic movement back to their engaged state. The ring 62 is thus again axially fixed to the plunger rod 6.

During the drug injection, the lug 64 has not moved inside the guiding path 70, and is still in the position illustrated in FIG. 11c.

When the patient removes the injection system 1 from the injection site and his/her fingers from the plunger rod 6, the force of the spring 21 causes the washer 63, collar 61, barrel flange 5, ring 62 and plunger rod 6 engaged with ring 62, as a whole, to move proximally towards a safety position, illustrated in FIGS. 13a-13e, in which the needle 4 is covered by the body 11 of the protective assembly 10. The ring 62 remains axially fixed to the plunger rod 6 due to the proximal portion 12 of body 11 which maintains the jaws 65 in the engaged state in the second complementary attaching element or attaching means 42.

During this movement, the coupling device 30 (i.e. ring 62 and collar 61) has deflected the safety arm 20 outwardly and has moved further distally, thereby allowing said safety arm 20 to move elastically back to its rest position in which it protrudes inwards, as shown in FIG. 13d.

Furthermore, the proximal tooth 15 of the body 11 has been deflected outwardly by an actuating member provided on the ring 62, namely the jaws 65, to allow the syringe 2 to move proximally beyond the storage position.

From the injection position to the storage position, the lug 64 of the collar 61 moves in the second portion 82 of the guiding path 70 provided in the body 11, from the point 83 up to the point 84 (FIG. 13e).

The ring 62, collar 61 and syringe 2 are maintained in the safety position relative to the body 11 by means of the proximal abutment 19 and the safety arm 20 (FIG. 13d), ensuring the needle 4 will remain covered by the body 11.

The invention is not limited to the embodiments described above by way of examples but it rather comprises all the technical equivalents and variants of the means described as well as their combinations.

The invention claimed is:

1. A protective assembly for a syringe comprising a barrel, a plunger rod and a needle, the protective assembly comprising:
   an axis;
   a body for receiving the syringe and extending along the axis; and
   a coupling device arranged inside the body, configured to be rigidly connected to the barrel as regards to axial movement relative to the body, the coupling device comprising an attaching element configured to be either in an engaged state with the plunger rod in order to axially fix the coupling device and the plunger rod, or in a release state in which the coupling device and the plunger rod are axially free relative to one another,
   wherein the coupling device is axially movable in the body from a storage position, distally along a first travel distance along which the attaching element is in the engaged state, to an injection position in which the needle extends beyond the body, and in which the attaching element is free to move towards the release state, and wherein the coupling device is axially movable in the body from the injection position, proximally towards a safety position, in which the needle is covered by the body, along a second travel distance along which the attaching element is in the engaged state.

2. The protective assembly according to claim 1, wherein the attaching element is elastically deformable from the engaged state to the release state.

3. The protective assembly according to claim 2, wherein the body includes an inner recess for allowing the attaching element to deflect outwardly towards the release state when the coupling device is in the injection position.

4. The protective assembly according to claim 2, wherein the attaching element is elastically deformable from the engaged state to the release state by being outwardly deflectable.

5. The protective assembly according to claim 1, wherein the attaching element comprises a plunger rod engaging portion configured to cooperate with the plunger rod.

6. The protective assembly according to claim 1, wherein the body comprises a holding element configured to maintain the attaching element in the engaged state when the coupling device moves from the storage position to the injection position, and when the coupling device moves from the injection position to the storage position.

7. The protective assembly according to claim 6, wherein the holding element comprises a stop surface arranged radially adjacent to the attaching element when the attaching element is in the engaged state, to prevent the attaching element from deflecting outwardly towards the release state.

8. The protective assembly according to claim 1, further comprising a distal axial blocking element for preventing distal movement of the coupling device relative to the body in the injection position.

9. The protective assembly according to claim 1, further comprising a biasing element configured to bias the coupling device relative to the body proximally from the injection position towards the safety position.

10. The protective assembly according to claim 1, wherein the body comprises a proximal tooth configured, when in a rest position, to prevent a proximal movement of the coupling device relative to the body from the storage position, and which is configured to deflect to allow the coupling device to move relative to the body from the injection position towards the safety position, beyond the storage position in the proximal direction.

11. The protective assembly according to claim 1, further comprising a blocking element of the coupling device in the safety position, the blocking element comprising at least one of:
   a proximal abutment; and at least one safety arm protruding inwards to form a distal abutment, and outwardly deflectable by the coupling device when the coupling device moves proximally towards the safety position.

12. The protective assembly according to claim 1, wherein the coupling device comprises a collar, and a ring which is distinct from the collar and which is arranged proximally from the collar, the ring comprising the attaching element.

13. The protective assembly according to claim 12, wherein one of the body and the collar comprises a guiding path and the other of the body and the collar comprises a lug engaged in the guiding path, the guiding path including a first portion which is tilted with respect to the axis, for guiding the lug when the coupling device moves from the storage position to the injection position, and a second portion which is parallel to the axis, for guiding the lug when the coupling device moves from the injection position to the safety position.

14. The protective assembly according to claim 12, wherein the collar is configured to rotate relative to the body about the axis.

15. The protective assembly according to claim 1, wherein the body has outwardly extending flanges on which a user can place his/her fingers.

16. An injection system comprising:
a syringe comprising a barrel, a plunger rod and a needle; and
a protective assembly according to claim 1, the barrel being supported by the coupling device.

17. The injection system according to claim 16, wherein the plunger rod includes:
a first complementary attaching element configured to cooperate with the coupling device attaching element when the coupling device moves from the storage position to the injection position; and
a second complementary attaching element which is distinct from the first complementary attaching element and located proximally from the first complementary attaching element, and which is configured to cooperate with the coupling device attaching element when the coupling device moves from the injection position to the safety position,
wherein at least one of the first or second complementary attaching element comprises a cavity for receiving a plunger rod engaging portion of the attaching element of the coupling device.

18. The injection system according to claim 16, wherein the body of the protective assembly comprises a proximal tooth configured, when in a rest position, to prevent a proximal movement of the coupling device relative to the body from the storage position, and which is configured to deflect to allow the coupling device to move relative to the body from the injection position towards the safety position, beyond the storage position in the proximal direction, and wherein the injection system further comprises an actuating member configured to deflect the proximal tooth of the body when the coupling device moves from the injection position towards the safety position.

19. A process for operating an injection system including:
a syringe comprising a barrel, a plunger rod and a needle; and
a protective assembly, the protective assembly comprising:
an axis;
a body for receiving the syringe and extending along the axis; and
a coupling device arranged inside the body, configured to be rigidly connected to the barrel as regards to axial movement relative to the body, the coupling device comprising an attaching element configured to be either in an engaged state with the plunger rod in order to axially fix the coupling device and the plunger rod, or in a release state in which the coupling device and the plunger rod are axially free relative to one another,
wherein the coupling device is axially movable in the body from a storage position, distally along a first travel distance along which the attaching element is in the engaged state, to an injection position in which the needle extends beyond the body, and in which the attaching element is free to move towards the release state, and
wherein the coupling device is axially movable in the body from the injection position, proximally towards a safety position, in which the needle is covered by the body, along a second travel distance along which the attaching element is in the engaged state, and wherein the barrel is supported by the coupling device of the protective assembly;
the process comprising:
placing the injection system in a storage position, with a distal end of the body in contact with an injection site;
pushing the plunger rod distally relative to the body to a position that is the most distal position of the plunger rod, thereby causing:
in a first phase, the barrel to move distally relative to the body, while the plunger rod does not axially move relative to the barrel, to cause the needle to extend beyond the body and prick the injection site thereby reaching an injection position at a distal most extension of the needle;
in a subsequent second phase, the plunger rod to move distally relative to the barrel, while the barrel does not axially move relative to the body, to cause injection; and
releasing the plunger rod and removing the injection system from the injection site, thereby enabling both the plunger rod and the barrel to move towards a safety position in which the needle is covered by the body.

* * * * *